United States Patent
Kimura et al.

(10) Patent No.: US 9,846,133 B2
(45) Date of Patent: Dec. 19, 2017

(54) SEMICONDUCTOR INSPECTION DEVICE INCLUDING A COUNTER ELECTRODE WITH ADJUSTABLE POTENTIALS USED TO OBTAIN IMAGES FOR DETECTION OF DEFECTS, AND INSPECTION METHOD USING CHARGED PARTICLE BEAM

(71) Applicant: Hitachi, Ltd., Chiyoda-ku, Tokyo (JP)

(72) Inventors: Yoshinobu Kimura, Tokyo (JP); Natsuki Tsuno, Tokyo (JP); Hiroya Ohta, Tokyo (JP); Renichi Yamada, Tokyo (JP); Toshiyuki Ohno, Tokyo (JP); Yuki Mori, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 14/443,720

(22) PCT Filed: Nov. 19, 2012

(86) PCT No.: PCT/JP2012/079892
§ 371 (c)(1),
(2) Date: May 19, 2015

(87) PCT Pub. No.: WO2014/076831
PCT Pub. Date: May 22, 2014

(65) Prior Publication Data
US 2015/0303030 A1 Oct. 22, 2015

(51) Int. Cl.
| | |
|---|---|
| G01N 23/225 | (2006.01) |
| H01J 37/28 | (2006.01) |
| G01N 23/22 | (2006.01) |
| H01J 37/22 | (2006.01) |
| H01L 21/66 | (2006.01) |
| H01J 37/285 | (2006.01) |
| H01L 21/67 | (2006.01) |
| H01J 37/147 | (2006.01) |
| H01L 29/16 | (2006.01) |

(52) U.S. Cl.
CPC ....... *G01N 23/225* (2013.01); *G01N 23/2208* (2013.01); *H01J 37/22* (2013.01);
(Continued)

(58) Field of Classification Search
CPC ..................................................... G01N 23/22
See application file for complete search history.

(56) References Cited

U.S. PATENT DOCUMENTS

| | | | | |
|---|---|---|---|---|
| 6,504,393 B1* | 1/2003 | Lo | ......................... | G01R 31/307 |
| | | | | 324/754.22 |
| 6,734,461 B1* | 5/2004 | Shiomi | .................... | C30B 23/00 |
| | | | | 257/194 |

(Continued)

FOREIGN PATENT DOCUMENTS

JP  2011-211035 A  10/2011

*Primary Examiner* — Jason McCormack
*Assistant Examiner* — James Choi
(74) *Attorney, Agent, or Firm* — Miles & Stockbridge P.C.

(57) ABSTRACT

Provided are an inspection device that detects with high precision and classifies surface unevenness, step batching, penetrating blade-shaped dislocations, penetrating spiral dislocations, basal plane dislocations, and stacking defects formed in an SiC substrate and an epitaxial layer; and a system. In the inspection device using charged particle beams, a device is used that has an electrode provided between a sample and an objective lens, the device applies a positive or negative voltage to the electrode and obtains images. A secondary electron emission rate is measured and energy EL and EH for the charged particles are found. A first image is obtained using the EH and positive potential conditions. A second image is obtained using the EL and negative potential conditions. A third image is obtained at the same position as the second image, and by using the EL and positive potential conditions.

4 Claims, 9 Drawing Sheets

(52) U.S. Cl.
CPC ............ *H01J 37/28* (2013.01); *H01J 37/285* (2013.01); *H01L 21/67288* (2013.01); *H01L 22/12* (2013.01); *H01J 37/1474* (2013.01); *H01J 2237/004* (2013.01); *H01J 2237/221* (2013.01); *H01J 2237/2806* (2013.01); *H01J 2237/2817* (2013.01); *H01L 29/1608* (2013.01); *H01L 2924/0002* (2013.01)

(56) References Cited

U.S. PATENT DOCUMENTS

| | | | |
|---|---|---|---|
| 2002/0166964 A1* | 11/2002 | Talbot | G06T 7/0004 250/307 |
| 2004/0087051 A1* | 5/2004 | Furuya | H01L 21/0242 438/47 |
| 2006/0243906 A1* | 11/2006 | Fukada | G01N 23/2251 250/307 |
| 2009/0085044 A1* | 4/2009 | Ohno | H01L 21/02378 257/77 |
| 2011/0155905 A1* | 6/2011 | Hatakeyama | H01J 37/244 250/307 |
| 2011/0242312 A1 | 10/2011 | Seki et al. | |
| 2012/0146056 A1* | 6/2012 | Momose | C30B 25/20 257/77 |
| 2014/0097342 A1* | 4/2014 | Tsuno | H01J 37/28 250/307 |
| 2016/0118217 A1* | 4/2016 | De | G01R 31/26 250/310 |

\* cited by examiner

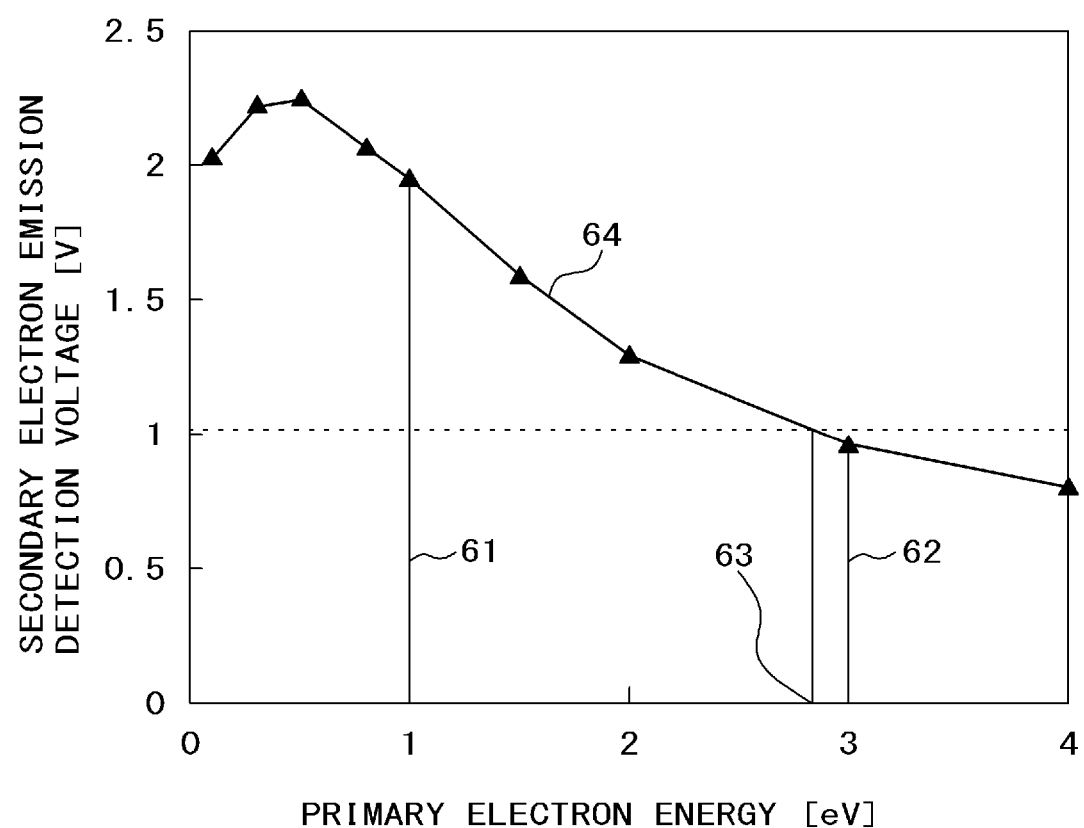

SEMICONDUCTOR INSPECTION DEVICE INCLUDING A COUNTER ELECTRODE WITH ADJUSTABLE POTENTIALS USED TO OBTAIN IMAGES FOR DETECTION OF DEFECTS, AND INSPECTION METHOD USING CHARGED PARTICLE BEAM

TECHNICAL FIELD

The present invention relates to a semiconductor inspection device and an inspection method using charged particle beam, in particular, pertaining to an inspection technique in terms of a semiconductor inspection device using charged particle beam by which defects of a single-crystal substrate, especially those of a silicon carbide substrate and the epitaxial layer formed on the silicon carbide substrate are detected and determined.

BACKGROUND ART

With the semiconductor devices formed with a semiconductor substrate in use, such defects of the semiconductor substrate as morphological defects such as concave and convex defects and crystal defects such as dislocations and stacking faults largely affect the performance, yielding and reliability of such devices. Such morphological defects and crystal defects are found especially on the silicon carbide substrate adopted for the semiconductor device for controlling power, so that it is extremely important that such substrate defects are inspected before such semiconductor device is manufactured. Thus, such inspection is performed in a non-destructive manner or on the premise that it does not affect the manufacturing steps of such semiconductor devices.

It is often that a silicon carbide substrate and a gallium nitride substrate are adopted for the materials of the above-mentioned semiconductor substrate. For the silicon carbide substrate, the silicon carbide substrate as it is or the substrate in which the epitaxial film made from the silicon carbide is formed on the silicon carbide substrate is often adopted. Further, for the gallium nitride, the substrate in which epitaxial growth of gallium nitride is performed on the silicone substrate is often adopted. Then, for such silicon carbide substrate and gallium substrate as well, it is important that their morphologic defects and crystal defects are inspected. Hereafter, the background art of the defects inspection of the silicon carbide substrate is described. To note, such background art also applies to the gallium substrate unless noted otherwise.

Then, as for the methods for inspecting such morphologic defects, such optical inspection methods are known as a differential interference contrast microscope method and a laser beam scattering method. Such inspection methods are also feasible to inspect even crystal defects just if there are morphologic features on the surface of a sample to be inspected (refer to Patent Literature 1 listed below). Further, as for the methods of inspecting such crystal defects, such methods are known as an X-ray topographic method, a transmission electron microscope method and an etch-pit method. However, the transmission electron microscope method and the etch-pit method lead to destroying a substrate, so that they are infeasible to apply for the non-destructive inspection adopted for a semiconductor substrate. Moreover, in the case of the methods where such defects are optically detected, the image resolution is susceptible to the restriction caused by the limit of wavelength of light.

CITATION LIST

Patent Literature

PTL 1: Japanese Patent Application Laid-Open No. 2011-211035

SUMMARY OF INVENTION

Technical Problem

As with such devices as semiconductor devices with such single-crystal substrate as made from silicon carbide and a single-crystal substrate in which an epitaxial layer is formed in use, in order to improve on the performance, yielding and reliability of such devices, it is required that such morphologic defects as concave and convex defects on the surface and step bunching as well as such crystal defects as penetrating dislocations and stacking faults be detected with high precision and classified into defect types for inspection. The defects inspection through such optical methods as mentioned above is based on signals showing morphologic anomaly.

As described above, the optical methods are feasible to inspect crystal defects just if there is morphologic anomaly on the surface as disclosed in Patent Literature 1, but they are infeasible to do so if there is no such anomaly thereon. As with such transmission electron microscope method and etch-pit method, they are feasible to inspect crystal defects with high sensitivity and high resolution, but cause a sample to be worked on or eroded in a chemical agent for etching for inspection, so that the problem with such methods lies in that such crystal defects cannot be inspected in a non-destructive manner.

The present invention is to provide an inspection device allowing such morphologic defects as concave and convex defects and step bunching as well as such crystal defects as penetrating spiral dislocations, blade-shaped dislocations and basal plane dislocations to be measured in a non-destructive manner.

Solution to Problem

The semiconductor inspection device according to the present invention comprises: a charged particle gun to generate a charged particle beam; a sample holder to support a sample; a deflection section to make the charged particle beam scanned to a surface of the sample; a detector to detect a secondary electron generated by the charged particle beam being irradiated onto the sample; an image processing section to process an output from the detector as an image; a sample potential controlling section to control a potential of the sample; a counter electrode disposed between the sample and an objective lens; a power source section to apply a positive potential or a negative potential with a potential of the sample defined as a reference to the counter electrode; an emissivity calculation section to calculate a secondary electron emissivity based on a current amount of the charged particle beam and the secondary electron; an energy calculation section to calculate a first incident energy in which the secondary electron emissivity is larger than 1 and a second incident energy in which the secondary electron emissivity is smaller than 1 based on an output of the emissivity calculation section; and a controlling section to control the first incident energy or the second incident energy and an application of the positive potential or the negative potential to the counter electrode based on measuring conditions for the sample.

Further, the inspection method for inspecting a single-crystal substrate or a substrate in which an epitaxial layer is formed according to the present invention comprises: a first step of applying a positive potential or a negative potential with a potential of the substrate defined as a reference to a counter electrode disposed between the substrate and an objective lens; a second step of calculating a secondary electron emissivity based on a current amount of a charged particle beam and a secondary electron; a third step of determining a first incident energy in which the secondary electron emissivity is larger than 1 and a second incident energy in which the secondary electron emissivity is smaller than 1; a fourth step of selecting either one of the positive and negative potentials at the first step and either one of the first and second incident energies at the third step; a fifth step, which is performed after the fourth step, of scanning the charged particle beam with regard to an inspection surface of the substrate and detecting a secondary electron: and a sixth step of inspecting a morphologic defect and a crystal defect of the substrate based on a scanned image obtained at the fifth step.

Advantageous Effects of Invention

According to the present invention, plural types of defects can be distinctly detected.

BRIEF DESCRIPTION OF DRAWINGS

FIG. 3 is a view to explain the first example of the present invention to define the electro-optical conditions EL and EH.

DESCRIPTION OF EMBODIMENTS

Hereinafter, the preferred embodiments of the present invention are explained with reference to the accompanying drawings. The present invention is applicable to the charged particle beam devices in general, but for the sake of explanations an electron beam device employing an electron which is one of the charged particles is described. Where it is more convenient to regard the electron beam device as a charged particle device in order to better understand the description of the present invention, you could refer to the description hereof with an electron replaced with a charged particle. To note, there is an ion besides an electron which are included in the charged particle, so that the present invention is also applicable to an ion beam device employing an ion.

Further, in the exampled presented herein, a silicon carbide substrate or a silicon carbide substrate in which an epitaxial layer of silicon carbide is formed is adopted for the single-crystal substrate to be inspected. Moreover, a substrate in which an epitaxial layer of gallium nitride is formed on the silicone substrate is also adoptable for the single-crystal substrate. Then, the secondary electron images of such single-crystal substrates and epitaxial layers are captured and defects are determined based on the contrasts of such images.

EXAMPLE 1

The inspection device according to the present invention as well as the present example according to the present invention exemplifying the means to define the electro-optical conditions (EH, EL, VP and VN) described below and the coordinates of a single-crystal substrate or a single-crystal substrate in which an epitaxial layer is formed are explained with reference to FIGS. 1 to 3.

Figure 1:
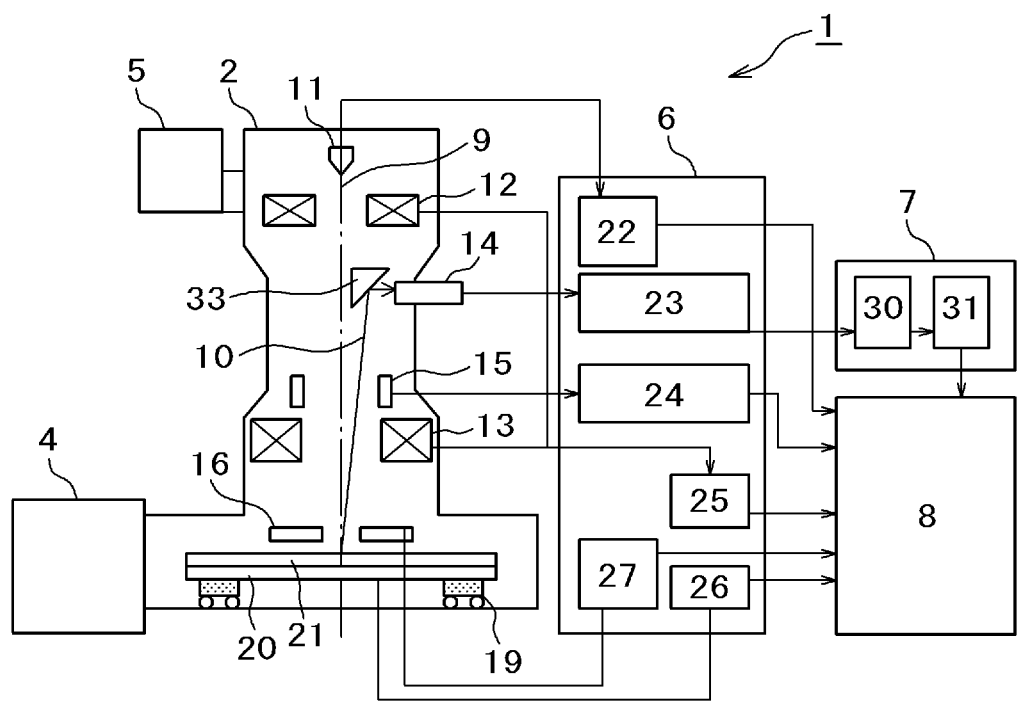
FIG. 1 is a structural view showing one example of a semiconductor inspection device according to the present invention.
Figure 2:
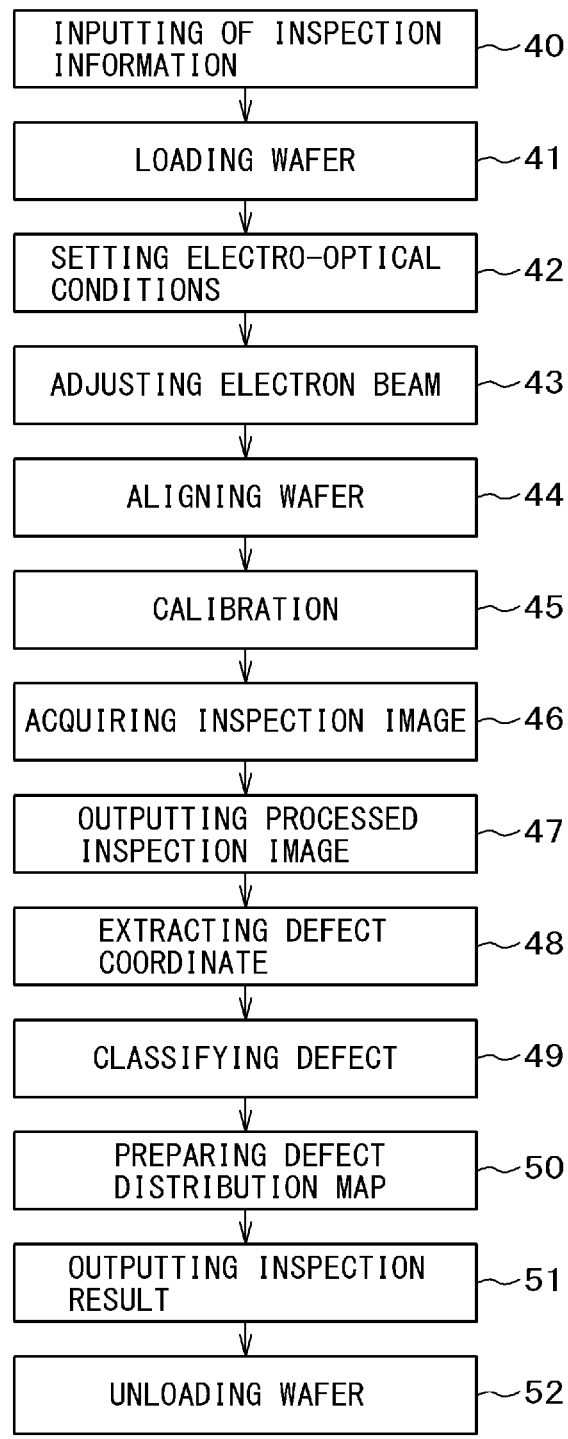
FIG. 2 is a view showing one example of the inspections steps according to the present invention

FIG. 1 is a structural view illustrating a standard inspection device by which a single-crystal substrate is inspected, which device comprises an electron gun 11; a deflector 15 to deflect a primary electron 9 emitted from the electron gun 11; an objective lens 13 to focus the primary electron; a counter electrode 16 to set a positive voltage (VP) or a negative voltage (VN) to control a secondary electron 10; a holder 20 to fix a single-crystal substrate 21 thereon to be inspected; an X-Y stage 19 to be moved to X and Y directions; a retarding voltage controlling section 27 to apply a retarding voltage (Vr) to the single-crystal substrate 21 to be inspected; a detector 14 to detect the secondary electron (backscattered electron) 10 generated by the irradiation of the primary electron 9; a detection system controlling section 23; an image processing circuit 30 to subject a detection signal detected by the detection system controlling section to an AD conversion in which the detection signal is converted into a digitalized image signal and then to process the digitalized image signal so as to determine a defect; an overall controlling section 31 to preserve information on the determined defect therein and to control the inspection device as a whole; and a console 8 to transmit a user's instruction to the entire controlling section.

Figure 9:
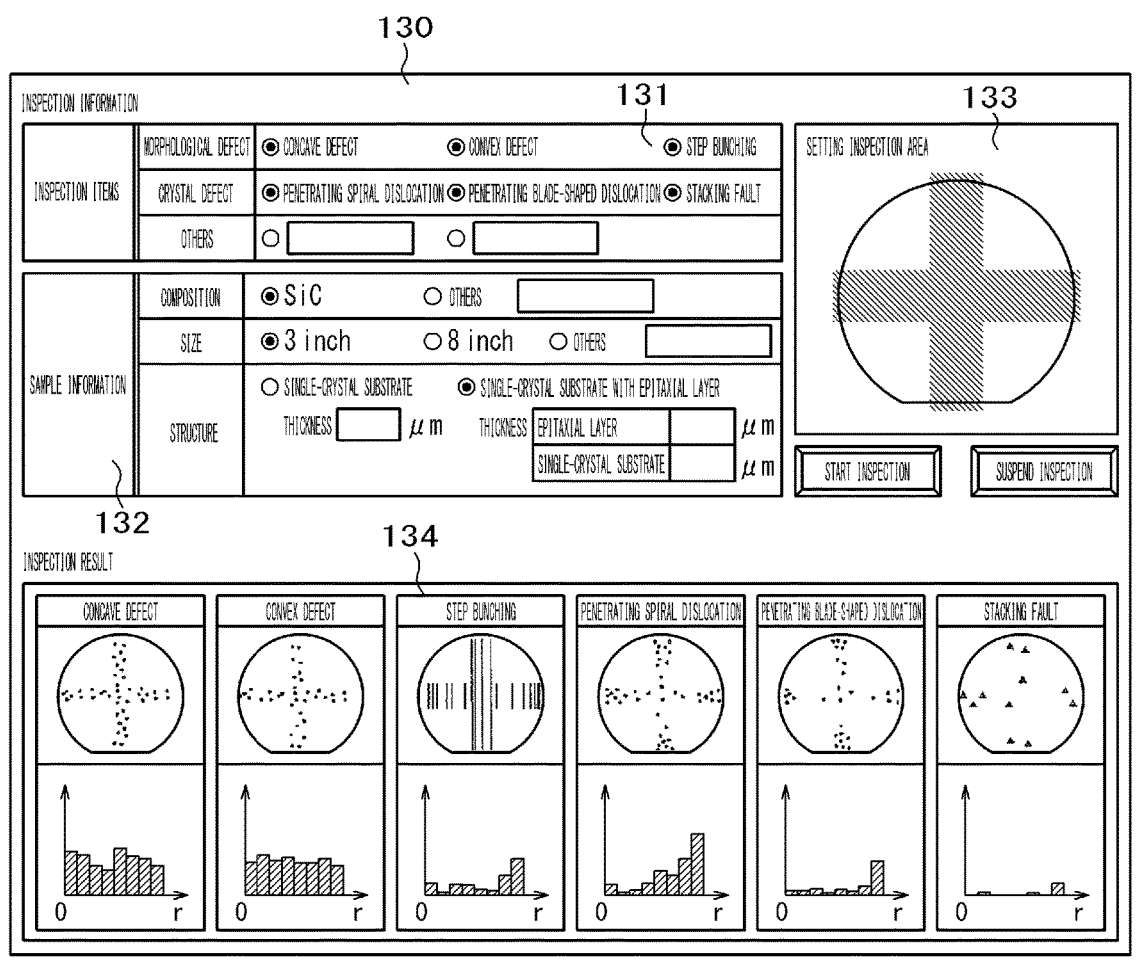
FIG. 9 is a view showing one example of GUI (Graphical User Interface) of the inspection device according to the present invention.

Then, with the inspection device according to the present invention in use, the inspection steps of a single-crystal substrate and a single-crystal substrate in which an epitaxial layer is formed are explained with reference to FIGS. 2, 3 and 9.

In the first place, inspection information is inputted at Step 40 to the console. The inputting step is performed trough GUI (Graphical User Interface) as shown in FIG. 9, in which inspection information 130 is displayed in the list through a pull-down menu, a check box 131 and as such or can be manually directly inputted.

In the inspection items, types of defects desired to be inspected, for instance, a concave defect on the surface, a convex defect on the surface, a step bunching, a penetrating spiral dislocation, a penetrating blade-shaped dislocation, a stacking fault and so forth are inputted. In addition, a user can voluntarily add defect items.

Then, in the sample information 132, the composition, the structure and the size of a substrate desired to be inspected as well as regarding the structure whether it is a single-crystal substrate or a single-crystal substrate in which an epitaxial layer is formed are inputted.

Next, inputting for setting an inspection area 133 is performed. The inspection area may be the entire surface of the substrate. Further, the area desired to be inspected is selectable through GUI. Moreover, coordinates can be directly input.

Subsequently, a substrate to be inspected is set on a wafer cassette 4 of the inspection device. One or plural sheets of substrates to be inspected can be set on the wafer cassette 4. To note, this setting operation may be performed prior to or posterior to the inputting of the inspection information.

Then, a wafer is loaded at Step 41 on the stage 20 of the inspection device.

Next, the electro-optical conditions are set at Step 42. Such electro-optical conditions include EH, EL, VP, VN described below and so forth. Then, these conditions are automatically defined based on the above-mentioned inspection information, which conditions may be manually inputted instead.

Then, the electron beam is adjusted at Step 43. The adjustment of the electron beam encompasses the adjustment of the optical axis, focusing adjustment, astigmatism adjustment and as such. The adjustment of the electron beam may be automatically performed instead.

Next, the alignment of the substrate to be inspected is performed at Step 44. The alignment is to align the coordinates (Xsub, Ysub) of the substrate to be inspected with those (Xs, Ys) of the stage.

Subsequently, calibration is performed at Step 45, in which how to decide the incident energy EH or EL is explained with reference to FIG. 3. For example, the electric current of the primary electron, the accelerating voltage Vp, and the retarding voltage Vr being defined as 100 pA, −10 kV and −9.7 kV respectively, a silicon dioxide film formed on a silicone substrate through thermal oxidation method and having one micron in thickness is adopted for a sample for calibration. The sample for calibration is placed on a part of the stage. For instance, it is placed on a corner portion of the stage. Then, to begin with, the primary electron beam is irradiated onto the sample for calibration. At this time, the silicon dioxide film is positively charged so that the secondary electron current tantamount to the current amount of the first electron is discharged. At this time, the gain and offset of the amplifier connected to the secondary electron detector are adjusted so that the output voltage of the amplifier results in being 1V, for example.

Then, the linearity of the detector is confirmed through the confirmation that the output voltage results in being 2V when the electric current of the primary electron is set at 200 pA and through the confirmation that the output voltage results in being 0.5V when the electric current of the primary electron is set at 50 pA. Where such linearity is not gained, the gain is adjusted such that the amplifier has an output voltage at which the linearity of the amplifier can be achieved. Through the above procedure, the current amount of the secondary electron can be converted from the output voltage of the secondary electron amplifier. The above calibration 45 can be performed through the recipe prepared by a user or automatically.

Next, the primary electron beam is irradiated onto the single-crystal substrate (silicon carbide substrate herein) to be inspected. With the accelerating voltage Vp defined as −10 kV and the retarding voltage Vr varied from −9.9V to 0V, the secondary electron current is measured. The measurement is performed manually or automatically. The secondary electron emissivity is given by the following fractional expression: secondary electron current/first electron current. The incident energy of the primary electron is given by the following expression: (Vr−Vp) electron Volt (eV).

FIG. 3 shows one example 64 in which the dependency of the secondary electron emissivity on the incident energy is plotted. The energy 63 of the primary electron by which the secondary electron emissivity becomes 1 is defined as the reference energy E2. Regarding the output signal voltage from the detector, its reference signal voltage is defined as 2V. The energy 62 higher than the reference voltage E2 is defined as EH while the energy 61 lower than the same is defined as EL.

Then, the potential VP of the counter electrode 16 is set at 2 kV for the secondary electron to be extracted to the detector side while the potential VN is set at (Vr−50V) for the secondary electron to be returned to the surface side.

Subsequently, an inspection image is acquired at Step 47. As for the inspection image, the stage is moved based on the inspection information; the primary electron beam 9 is deflected in the X and Y directions through the defector 15; and a secondary electron signal is acquired in synchronization with the deflection of the primary electron beam, thereby, the inspection image being acquired at Step 46. Moving the stage and deflecting the primary electron beam may be performed independently or associatively. Hereupon, with a reference point preliminarily set on the substrate to be inspected, the stage coordinates (Xs, Ys) are aligned with the primary electron scanning coordinates (Xe, Ye), thereby, the substrate coordinates (Xsub, Ysub) being given by (Xs+Xe, Ys+Ye).

Then, a processed inspection image in which the inspection image is subjected to image processing through a threshold filter is outputted at Step 47 based on the above-mentioned reference signal voltage.

Next, based on the inspection information, the inspection image and the processed inspection image with the electro-optical conditions modified are acquired, in which the figures corresponding to defects are acquired and such defect coordinates as vertex coordinates and barycentric coordinates are extracted at Step 48.

Then, the defect figures are acquired from the subtracted image among different inspection images.

Next, the defects are classified through the pattern recognition of the defect figures at Step 49.

Subsequently, the distribution map is automatically prepared for the respective defects at Step 50. The aforementioned operations of outputting processed inspection image, extracting figures, classifying defects and preparing the distribution map can be also processed with a computer incorporated in the inspection device according to the present invention. Further, such operations can be processed with a computer connected through a network. Moreover, a plurality of substrates to be inspected can be inspected in parallel with a plurality of inspection devices connected to one another through a network. After the inspection result is outputted at Step 51, the inspected substrate is unloaded at Step 52. When there are substrates to be inspected in succession, a wafer is loaded on the stage and subjected to the above-mentioned inspection steps.

EXAMPLE 2

The methods which determine and detect a concave defect and a convex defect of the single-crystal substrate to be inspected with the inspection device according to Example 1 in use is explained with reference to FIGS. 4A to 4D as well as FIG. 5A to 5D.

The energy EH of the primary electron is set at 3 kV while the potential VP of the counter electrode 16 is set at 2 kV and the primary electron beam 9 is deflected in the X and Y directions with the deflector 15 so that the surface of the substrate 21 to be inspected is scanned. In synchronization with the scanning operation by the primary electron beam 9, the secondary electron signal 10 is acquired.

With a reference point preliminarily set on the substrate to be inspected, the stage coordinates (Xs, Ys) are aligned with the primary electron scanning coordinates (Xe, Ye), thereby, the substrate coordinates (Xsub, Ysub) being given by (Xs Xe, Ys+Ye).

Figure 4A:
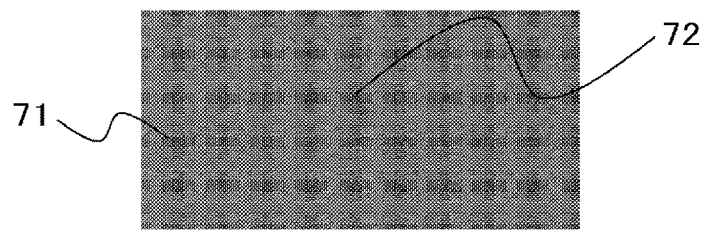
FIG. 4A is a view to explain the second example of the present invention in which a convex defect is inspected.
Figure 4B:
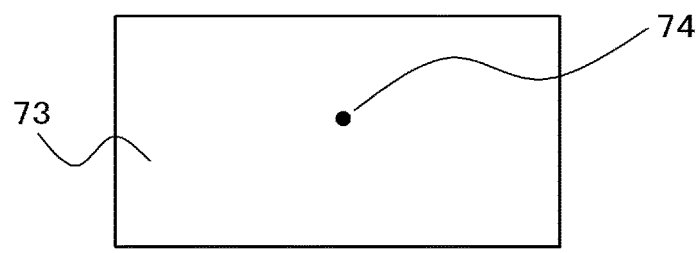
FIG. 4B is a view to explain the second example of the present invention in which a convex defect is inspected.
Figure 4C:
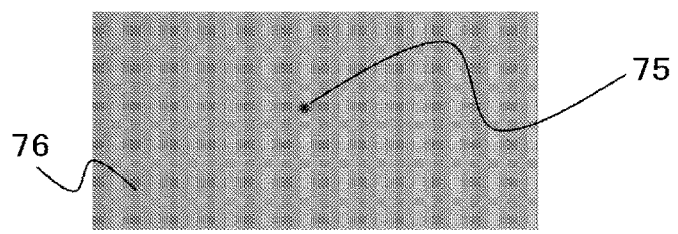
FIG. 4C is a view to explain the second example of the present invention in which a convex defect is inspected.
Figure 4D:
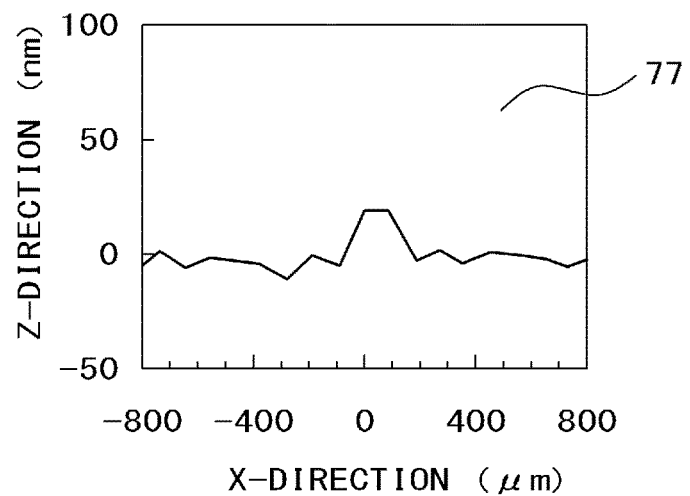
FIG. 4D is a view to explain the second example of the present invention in which a convex defect is inspected.

FIG. 4A shows the first inspection image 71 of the substrate which is scanned by the primary electron beam. The dark dot 72 illustrated therein is a convex defect. In order to explain the reason such dot is determined as a convex defect, a laser scanning microscope image 76 of the same spot is shown in FIG. 4C. The laser scanning microscope image is a dark dot 75, and it can be confirmed in FIG. 4D that the profile 77 in the vicinity of the dark dot 75 is convexly plotted.

Figure 5A:
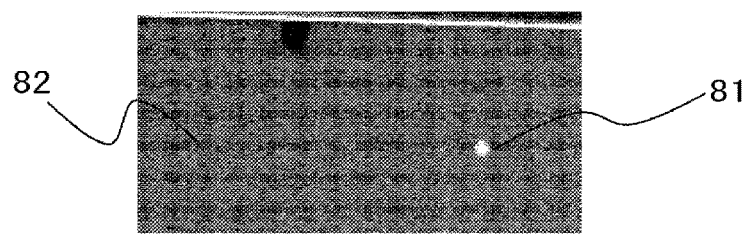
FIG. 5A is a view to explain the second example of the present invention in which a concave defect is inspected.
Figure 5B:
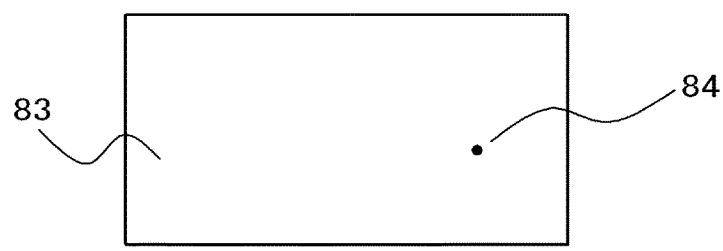
FIG. 5B is a view to explain the second example of the present invention in which a concave defect is inspected.
Figure 5C:
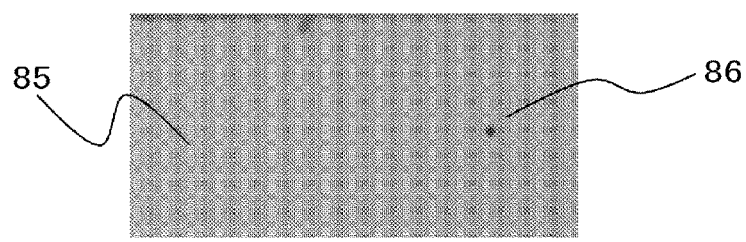
FIG. 5C is a view to explain the second example of the present invention in which a concave defect is inspected.
Figure 5D:
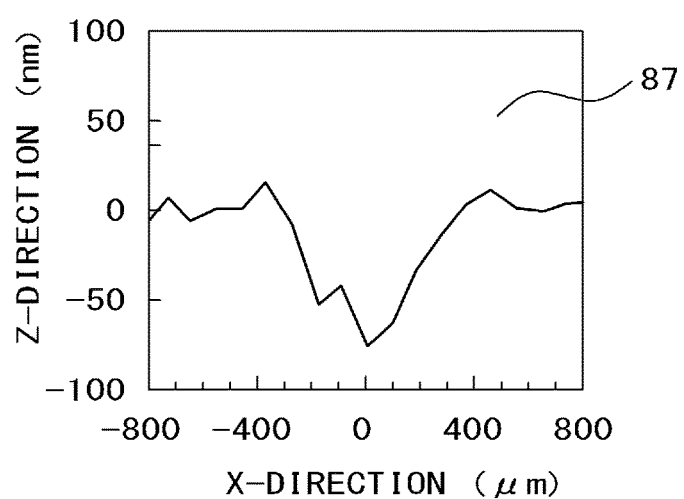
FIG. 5D is a view to explain the second example of the present invention in which a concave defect is inspected.

FIG. 5A shows the first inspection image 82 of the substrate at the spot different from that shown in FIG. 4A. A bright dot 81 shown in FIG. 5A is a concave defect. In order to explain the reason such dot is a concave defect, a laser scanning microscope image 85 of the same spot is shown in FIG. 50. The laser scanning microscope image is a dark dot 86 and it can be confirmed in FIG. 5D that the profile 87 in the vicinity of the dark dot 86 is concavely plotted. The confirmation of the concave and convex shapes according to the present example is feasible also through the cross-sectional observation of the substrate employing a scanning electron microscope. Regarding the output signal voltage from the detector, its reference signal voltage is 2V. The processed inspection image (1A) obtained by subjecting the output signal voltage of 2.5V or higher to the threshold filter is shown by the reference numeral 83 in FIG. 5B. The dot-shaped FIG. 84 is a concave defect. Further, the processed inspection image (1B) obtained by subjecting the output signal voltage of 1.5V or lower to the threshold filter is shown by the reference numeral 73 in FIG. 4B. The dot-shaped FIG. 74 is a convex defect. Accordingly, by extracting the dot-shaped figures contained in the processed inspection images (1A) and (1B), the defect distribution among those concave and convex defects is obtained.

EXAMPLE 3

The methods which determine a penetrating dislocation, a basal plane dislocation and a stacking fault with the inspection device according to Example 1 in use is explained with reference to FIGS. 6 and 7.

In order to make the energy EL of the primary electron 1 keV, the accelerating voltage Vp and the retarding voltage Vr are defined as −10 kV and −9 kV respectively. The potential VN of the counter electrode 16 is defined as −9.05 kV. The primary electron beam 9 is deflected in the X and Y directions with the deflector 15 so that the surface of the substrate to be inspected is scanned. In synchronization with the scanning operation by the primary electron beam, the secondary electron signal 10 is acquired.

With a reference point preliminarily set on the substrate to be inspected, the stage coordinates (Xs, Ys) are aligned with the primary electron scanning coordinates (Xe, Ye), thereby, the substrate coordinates (Xsub, Ysub) being given by (Xs+Xe, Ys+Ye). The second inspection images as acquired are shown by the reference numeral 101 in FIG. 6A and by the reference numeral 110 in FIG. 7A.

Figure 6A:
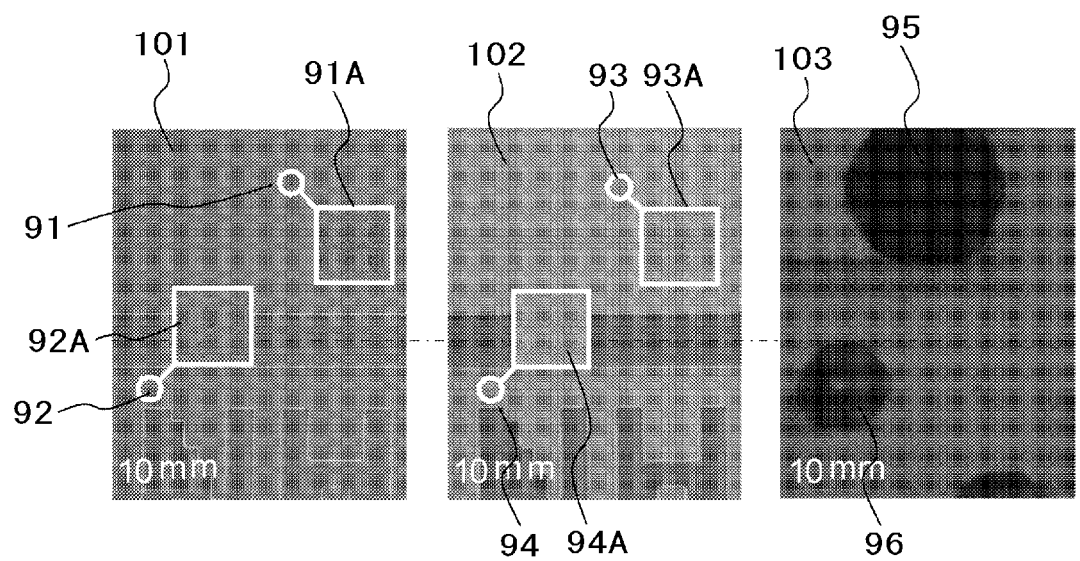
FIG. 6A is a view to explain the fourth example in which a penetrating spiral dislocation and a penetrating blade-shaped dislocation are inspected.
Figure 6B:
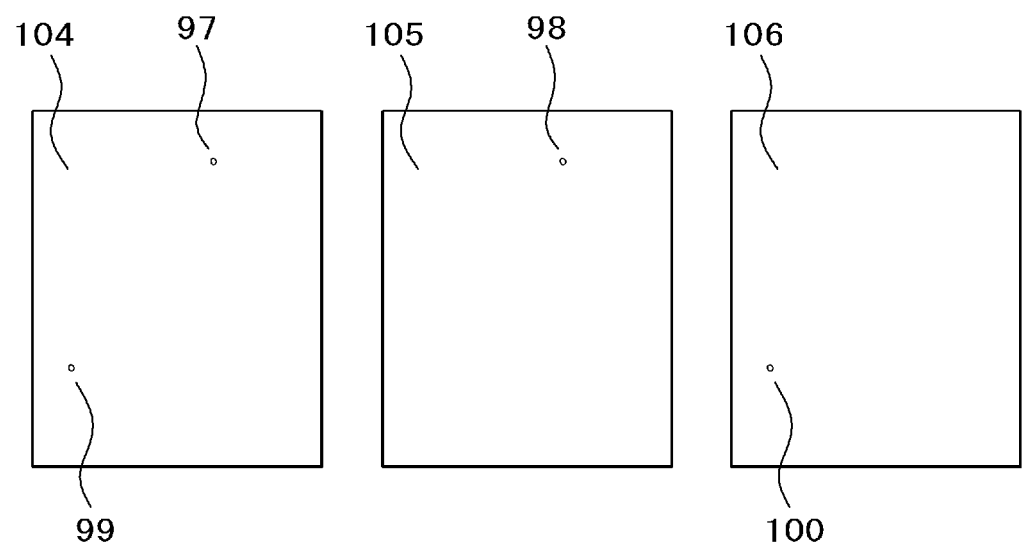
FIG. 6B is a view to explain the fourth example in which a penetrating spiral dislocation and a penetrating blade-shaped dislocation are inspected.
Figure 7A:
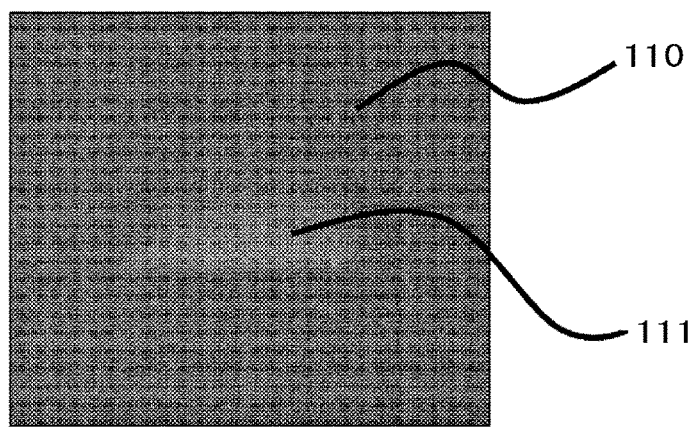
FIG. 7A is a view to explain the third example of the present invention in which a stacking fault is inspected.
Figure 7B:
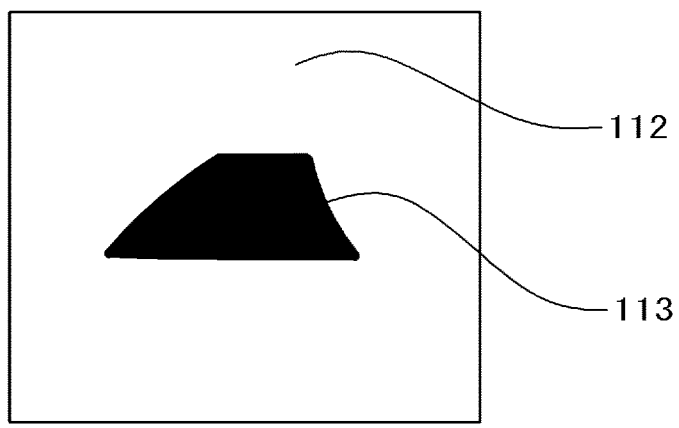
FIG. 7B is a view to explain the third example of the present invention in which a stacking fault is inspected.
Figure 7C:
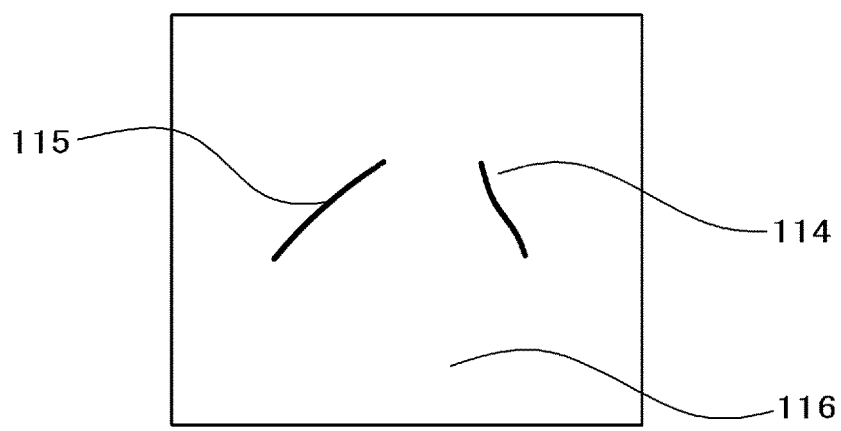
FIG. 7C is a view to explain the third example of the present invention in which a stacking fault is inspected.

The second inspection images shown in FIG. 6A and FIG. 7A are captured at different inspection areas. The substrate is subjected to patterning with lithography in order to make the correspondence of defect spots easy to observe in the second inspection images 101 and 102. Dark dots 91 and 92 are observed in the second inspection image 101. The reference sign 91A is an enlarged view of the dark dot 91 which is inserted in the image 101 to make such dark dot easy to observe. The reference sign 92A is an enlarged view of the dark dot 92 which is inserted in the image 101 to make such dark dot easy to observe.

Then, the following image processing is performed. Regarding the output signal voltage from the detector, its reference signal voltage is 2V. The processed inspection image (2A) obtained with the output signal voltage of 2.5V or higher subjected to the threshold filter is shown by the reference numeral 112 in FIG. 7B. The trapezoidal figure 113 is extracted from the processed inspection image (2A) 112. The inside of the trapezoidal figure 113 corresponds to a stacking fault. The lateral side line components 115 and 114 shown in FIG. 7C of the trapezoid contouring the trapezoidal figure 113 contained in the processed inspection image (2A) 112 correspond to basal plane dislocations. Further, the processed inspection image (2B) obtained with the output signal voltage of 1.5 v or lower subjected to the threshold filter is shown by the reference numeral 104 in FIG. 6B. The dot-shaped FIGS. 97 and 99 correspond to penetrating dislocations.

As described above, the distribution of the defects or the penetrating dislocations, the basal plane dislocations and the stacking faults on the substrate can be obtained through extracting figures contained in the respective processed inspection images and classifying such figures accordingly.

EXAMPLE 4

The methods which determine the penetrating spiral dislocation and the penetrating blade-shaped dislocation with the inspection device according to Example 1 in use is explained with reference to FIG. 6.

In order to make the energy EL of the primary electron 1 keV, the accelerating voltage Vp and the retarding voltage Vr are defined as −10 kV and −9 kV respectively. The potential VP of the counter electrode 16 is defined as 2 kV. The primary electron beam 9 is deflected in the X and Y directions with the deflector 15 so that the surface of the substrate 21 to be inspected is scanned. In synchronization with the scanning operation by the primary electron beam, the secondary electron signal 10 is acquired.

Further, with a reference point preliminarily set on the substrate to be inspected, the stage coordinates (Xs, Ys) are aligned with the primary electron scanning coordinates (Xe, Ye), thereby, the substrate coordinates (Xsub, Ysub) being given by (Xs+Xe, Ys+Ye). The third inspection image as acquired is shown by the reference numeral 102 in FIG. 6A. The third inspection image 102 and the second inspection image 101 are captured at the same inspection area.

Then, the following image processing is performed. Regarding the output signal voltage from the detector 14, its reference signal voltage is 2V. The third processed inspection image with the output signal voltage of 1.5V or lower subjected to the threshold filter is shown by the reference numeral 105 in FIG. 6B. The dot-shaped FIG. 98 contained in the third processed inspection image 105 corresponds to a penetrating spiral dislocation. Further, the subtracted image between the second processed inspection image 104 and the third processed inspection image 105 is defined as the fourth processed inspection image 106 and the dot-shaped figure 100 contained in the image 106 corresponds to a penetrating blade-shaped dislocation. In order to confirm the accuracy of determining such dislocations hereof, the substrate to be inspected is subjected to etching with potassium hydroxide and the resulting state thereof is checked.

The reference numeral 103 in FIG. 103A shows an optical microscopic image of the substrate subjected to etching. According to the etch-pit method, the penetrating spiral dislocation with the reference numeral 95 can be distinguished from the penetrating blade-shaped dislocation with the reference numeral 96 from the etch-pit configurations. As described above, according to the present example, the distribution map of the defects or the penetrating spiral dislocations and the penetrating blade-shaped dislocations on the substrate can be obtained.

EXAMPLE 5

Figure 8A:
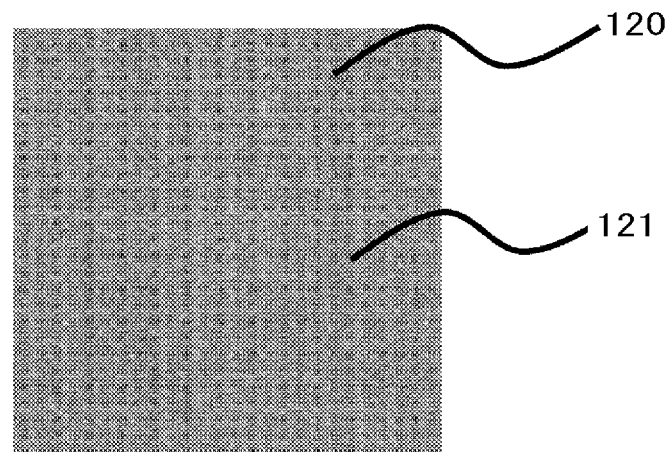
FIG. 8A is a view to explain the fifth example of the present invention in which a step bunching is inspected.
Figure 8B:
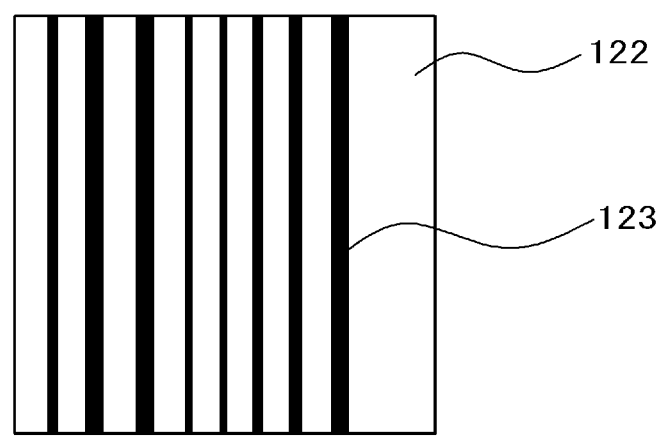
FIG. 8B is a view to explain the fifth example of the present invention in which a step bunching is inspected.

The methods which determine a step bunching with the inspection device according to Example 1 in use is explained with reference to FIGS. 8A and 8B.

In order to make the energy EL of the primary electron 1 keV, the accelerating voltage Vp and the retarding voltage Vr are defined as −10 kV and −9 kV respectively. The potential VN of the counter electrode 16 is defined as −9.05 kV. The primary electron beam 9 is deflected in the X and Y directions with the deflector 15 so that the surface of the substrate 21 to be inspected is scanned. In synchronization with the scanning operation by the primary electron beam 9, the secondary electron signal 10 is acquired.

With a reference point preliminarily set on the substrate to be inspected, the stage coordinates (Xs, Ys) are aligned with the primary electron scanning coordinates (Xe, Ye), thereby, the substrate coordinates (Xsub, Ysub) being given by (Xs+Xe, Ys+Ye). The second inspection image as acquired is shown by the reference numeral 120 in FIG. 8A.

Then, the following image processing is performed. Regarding the output signal voltage from the detector 14, its reference signal voltage is 2V. The processed inspection image (2B) obtained with the output signal voltage of 1.5V or lower subjected to the threshold filter is shown by the reference numeral 122 in FIG. 8B. The sash-shaped figure 123 contained in the processed inspection image (2B) corresponds to a step bunching. As described above, according to the present example, the distribution map of the defect or the step bunching on the substrate can be obtained.

EXAMPLE 6

The present example is to explain how to output the distribution data of the defects on the substrate to be inspected with in use the inspection device according to Example 1 and the methods of determining the defects according to Examples 2 to 5.

The first, second and third inspection images are acquired with in use the inspection device according to Example 1 with its inspections steps as well as the electro-optical conditions explained in Examples 2 to 5; with those images subjected to the image processing the processed inspection image (1A), the processed inspection image (1B), the processed inspection image (2A), the processed inspection image (2B), the third processed inspection image and the fourth processed inspection image are acquired; and figures contained in those processed images are extracted through pattern recognition and classified accordingly.

Since there are contained pieces of coordinate information in such figures, the planar distribution of such morphological defects as a concave defect, a convex defect, a step bunching as well as such crystal defects as a penetrating spiral dislocation, a penetrating blade-shaped dislocation and a stacking fault can be acquired. The inspection result can be either expressed with a map shown by the reference numeral 134 in FIG. 9 or be outputted with a table format.

EXAMPLE 7

The present example is to explain how to output the quality of the substrate to be inspected with in use the planar distribution of the defects explained in Example 6. To begin with, a quality-based unit area is inputted. Based on such unit area, a map is prepared with the meshes in which the substrate is segmented in a rectangular shape. A defect density is calculated from the number of defects per mesh.

A substrate map in which a defect density per mesh is shown is outputted. Further, the meshes in which the substrate is concentrically segmented may be adopted for the above-mentioned meshes.

In the same way, a defect density is calculated from the number of defects per mesh. The defect density in the radius direction from the center of the substrate is outputted. The quality of the substrate can be quantified from the above-mentioned defect density.

EXAMPLE 8

The present example is to explain the methods which determine whether or not the epitaxial growth is conditionally available with the quality-based quantification of the substrate according to Example 6 in use. In the first place, the substrate is inspected according to Example 6 so that a set of data A containing the inspection result is acquired.

Then, an epitaxial layer is grown on such substrate. The substrate in which such epitaxial layer is formed is inspected with the method according to Example 6 in use; a set of data B containing the inspection result is acquired; and the set of data A is compared with the set of data B, thereby, whether or not the epitaxial growth is conditionally available being determined.

EXAMPLE 9

Adopting a scanning electron microscope comprising a detector to detect an electron backscattered pattern, an X-ray detector and so forth for the inspection device according to Example 1 allows defects to be observed along with their physical analysis with the methods explained in Examples 2 to 5 in use.

As described above, the present invention permits a concave or convex defect, a step bunching, a spiral dislocation, a blade-shaped dislocation, a basal plane dislocation and a stacking fault which are formed on a single-crystal substrate and an epitaxial layer to be detected as well as provides defects inspection by which such defects can be distinctly detected with high precision and classified accordingly.

REFERENCE SIGNS LIST

1: electron beam device,
2: electro-optical system,
3: stage mechanism system,
4: wafer carriage system,
5: vacuum exhaustion system,
6: controlling system,
7: image processing system,
8: operating section,
9: primary electron,
10: secondary electron,
11: electron gun,
12: condenser lens.
13: objective lens,
14: secondary electron detector,
15: deflector,
16: counter electrode,
19: X-Y stage,
20: wafer holder,
21: wafer,
22: electron beam controlling section,
23: detection system controlling section,
24: deflection controlling section,
25: electron lens controlling section,
26: retarding voltage controlling section,
27: electrode controlling section,
30: image processing section,
31: image storage section,
33: reflection plate,
40: inputting step of inspection information,
41: step of loading wafer,
42: step of setting electro-optical conditions,
43: step of adjusting electron beam,
44: step of aligning wafer,
45: calibration step,
46: step of acquiring inspection image,
47: step of outputting processed inspection image,
48: step of extracting defect coordinate,
49: step of classifying defects,
50: step of preparing defect distribution map,
51: step of outputting inspection result,
52: step of unloading wafer,
61: EL
62: EH
63: E2
64: secondary electron emissivity curve,
71: first inspection image,
72: dot-shaped defect,
73: processed inspection image (1A),
74: inspected figure showing convex defect,
75: laser microscope contrast of defect,
76: laser microscopic image,
77: laser microscope line profile of defect portion,
81: dot-shaped defect,
82: first inspection image,
83: processed inspection image (1B),
84: inspected figure showing concave defect,
85: laser microscopic image,
86: laser microscope contrast of defect portion,
87: laser microscope line profile of defect portion,
91: dot-shaped defect,
91A: enlarged view of dark dot 91 which is inserted in image 101,
92: dot-shaped defect,
93: dot-shaped defect,
93A: enlarged view of dark dot 93 which is inserted in image 102,
94: contrast of dot-shaped defect 92 at same spot
94A: enlarged view of dark dot 94 which is inserted in image 102,
95: etch-pit showing penetrating spiral dislocation,
96: etch-pit showing penetrating blade-shaped dislocation,
97: inspected figure showing penetrating spiral dislocation,
98: inspected figure showing penetrating spiral dislocation,
99: inspected figure showing penetrating blade-shaped dislocation,
100: inspected figure showing penetrating blade-shaped dislocation,
101: second inspection image,
102: third inspection image,
103: optical microscopic image of substrate subjected etching with potassium hydroxide
104: processed inspection image (2B),
105: third processed inspection image,
106: fourth processed inspection image,
110: second inspection image,
111: trapezoidal defect,
112: processed inspection image (2A),
113: inspected figure showing stacking fault,
114: inspected figure showing basal plane dislocation,
115: inspected figure showing basal plane dislocation,
116: processed inspection image where lateral sides of trapezoid are extracted from processed inspection image (2A),
120: second inspection image,
121: contrast of sash-shaped defect,
122: processed inspection image (2A),
123: inspected figure showing step bunching,
130: inspection information,
131: column where inspection items are inputted,
132: column where structure of substrate to be inspected is inputted,
133: column where inspection area is set,
134: inspection result

The invention claimed is:
1. A semiconductor inspection device, comprising:
a charged particle gun to generate a charged particle beam;
a sample holder to support a sample;
a deflector to deflect the charged particle beam to a surface of the sample;
a detector to detect a secondary electron generated by the charged particle beam being irradiated onto the sample;

an image processing circuit to process an output from the detector as an image;

a sample potential controller to control a potential of the sample;

a counter electrode disposed between the sample and an objective lens;

a power source to apply one of a positive potential and a negative potential to the counter electrode and to apply a potential of the sample defined as a reference to the counter electrode;

an emissivity calculator to calculate a secondary electron emissivity based on a current amount of the charged particle beam and the secondary electron;

an energy calculator to calculate a first incident energy in which the secondary electron emissivity is larger than 1 and a second incident energy in which the secondary electron emissivity is smaller than 1 based on an output of the emissivity calculator; and an electrode controller controlling one of the first incident energy and the second incident energy and an application of one of the positive potential and the negative potential to the counter electrode based on measuring conditions for the sample, wherein the electrode controller controls (i) the semiconductor inspection device under a first condition that the incident energy results in being the second incident energy and the application of the potential to the counter electrode results in being the negative potential, and (ii) the semiconductor inspection device under a second condition that the incident energy results in being the second incident energy and the application of the potential to the counter electrode results in being the positive potential; and the image processing circuit acquires a first image under the first condition and a second image under the second condition and determines a penetrating blade-shaped dislocation contained in a subtracted image between the first and second images by distinguishing the penetrating blade-shaped dislocation in one of the first and second images from other defects in both of the first and second images using pattern recognition.

2. The semiconductor inspection device according to claim 1, further comprising:

an inspection items input section in which types of morphological defects or crystal defects of the sample as the measuring conditions for the sample are inputted, the electrode controller controlling the semiconductor inspection device under one of the first incident energy and the second incident energy and the application of one of the positive potential and the negative potential to the counter electrode based on the inputted types; and the image processing circuit being characterized by making decision on the morphological defect and the crystal defect of the sample based on a plurality of images obtained by the control.

3. The semiconductor inspection device according to claim 2 characterized in that the sample is one of a single-crystal substrate and a substrate in which an epitaxial layer is formed, the image processing circuit being characterized by quantifying quality of the substrate based on the decision on the morphological defect and the crystal defect of the sample and outputting the quantified quality.

4. An inspection method for inspecting a single-crystal substrate or a substrate in which an epitaxial layer is formed, the inspection method being characterized by comprising:

a first step of applying one of a positive potential and a negative potential with a potential of the substrate defined as a reference to a counter electrode disposed between the substrate and an objective lens;

a second step of calculating a secondary electron emissivity based on a current amount of a charged particle beam and a secondary electron;

a third step of determining a first incident energy in which the secondary electron emissivity is larger than 1 and a second incident energy in which the secondary electron emissivity is smaller than 1;

a fourth step of selecting either one of the positive and negative potentials at the first step and either one of the first and second incident energies at the third step;

a fifth step, which is performed after the fourth step, of scanning the charged particle beam with regard to an inspection surface of the substrate and detecting a secondary electron; and a sixth step of inspecting a morphologic defect and a crystal defect of the substrate based on a scanned image obtained at the fifth step, wherein at the fourth step, (i) under a first condition, the second incident energy and the application of the negative potential to the counter electrode results are selected, and (ii) under a second condition, the second incident energy and the application of the positive potential to the counter electrode results are selected; and a first image is acquired under the first condition and a second image is acquired under the second condition and a penetrating blade-shaped dislocation contained in a subtracted image between the first and second images is determined by distinguishing the penetrating blade-shaped dislocation in one of the first and second images from other defects in both of the first and second images using pattern recognition.

* * * * *